(12) United States Patent
Klosin et al.

(10) Patent No.: US 10,183,924 B2
(45) Date of Patent: Jan. 22, 2019

(54) SULFONYLAZIDE DERIVATIVE FOR DIENE POLYMER

(71) Applicant: Dow Global Technologies LLC, Midland, MI (US)

(72) Inventors: Jerzy Klosin, Midland, MI (US); Adriana I. Moncada, Midland, MI (US); Brian W. Walther, Freeport, TX (US); Michael D. Read, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 9 days.

(21) Appl. No.: 15/383,232

(22) Filed: Dec. 19, 2016

(65) Prior Publication Data

US 2017/0190823 A1 Jul. 6, 2017

Related U.S. Application Data

(60) Provisional application No. 62/379,328, filed on Aug. 25, 2016, provisional application No. 62/272,851, filed on Dec. 30, 2015.

(51) Int. Cl.
*C08F 279/02* (2006.01)
*C07D 307/89* (2006.01)

(52) U.S. Cl.
CPC .......... *C07D 307/89* (2013.01); *C08F 279/02* (2013.01); *C08F 2500/17* (2013.01); *C08F 2500/18* (2013.01); *C08F 2800/20* (2013.01)

(58) Field of Classification Search
CPC ................ C08F 279/00; C08F 2500/17; C08F 2500/18; C08F 2500/20; C07D 307/89
See application file for complete search history.

(56) References Cited

U.S. PATENT DOCUMENTS

| | | | |
|---|---|---|---|
| 3,701,788 A | 10/1972 | Sayigh et al. | |
| 4,031,068 A | 6/1977 | Cantor | |
| 4,174,358 A | 11/1979 | Epstein | |
| 4,515,636 A | 5/1985 | Carney et al. | |
| 4,861,843 A | 8/1989 | Udding | |
| 5,356,999 A * | 10/1994 | Kapuscinski et al. | C10M 151/02 525/286 |
| 6,331,597 B1 | 12/2001 | Drumright et al. | |
| 6,521,306 B1 | 2/2003 | Hoenig et al. | |
| 7,399,808 B2 | 7/2008 | Walters et al. | |
| 2002/0156193 A1 | 10/2002 | Tau et al. | |
| 2013/0092590 A1 | 4/2013 | Bellini et al. | |

FOREIGN PATENT DOCUMENTS

EP 0834415 A2 4/1998

* cited by examiner

*Primary Examiner* — Nathan M Nutter
(74) *Attorney, Agent, or Firm* — Husch Blackwell LLP

(57) ABSTRACT

The present disclosure provides a composition. In an embodiment, a composition is provided and includes an ethylene/α-olefin/diene terpolymer and a polar component. The composition also includes a sulfonamide phthalic anhydride linkage (SPA) bonding the ethylene/α-olefin/diene terpolymer to the polar component.

14 Claims, No Drawings

US 10,183,924 B2

SULFONYLAZIDE DERIVATIVE FOR DIENE POLYMER

BACKGROUND

The present disclosure relates to compositions composed of grafted diene polymer and processes for producing the same.

Known are maleic anhydride (MAH) grafted olefin-based polymer resins (MAH-g-PO). Such resins are commonly used as tie layer in multilayer films for food packaging and specialty packaging. The MAH-g-PO tie layer is typically used to bind a polyolefin layer to other layers containing a polar substrate, such as nylon, for example. Currently, MAH-g-PO resin is produced via free radical grafting of maleic anhydride onto polyolefin in a melt blend process.

The art recognizes the benefits of MAH grafted ethylene/α-olefin/diene terpolymer. However, free radical grafting of an ethylene/α-olefin/diene terpolymer is problematic because the resultant MAH-g-ethylene/α-olefin/diene terpolymer has insufficient flow at elevated temperature (i.e., temperature above ambient) and low tensile strength. In addition, when the ethylene/α-olefin/diene terpolymer contains propylene comonomer, undesired chain scission side reactions (resulting in lower molecular weight and higher melt flow rate) occur during free radical grafting.

Desirable would be an ethylene/α-olefin/diene terpolymer with MAH functionalization that is flowable at elevated temperature and is not subject to crosslinking and/or chain scission during the production thereof.

SUMMARY

The present disclosure provides a composition. In an embodiment, a composition is provided and includes an ethylene/α-olefin/diene terpolymer and a polar component. The composition also includes a sulfonamide phthalic anhydride linkage (SPA) bonding the ethylene/α-olefin/diene terpolymer to the polar component.

The present disclosure provides another composition. In an embodiment, a composition is provided and includes an ethylene/α-olefin/diene terpolymer, a first polar polymer, and a second polar polymer different than the first polar polymer. The composition also includes a first sulfonamide phthalic anhydride (SPA) linkage bonding the ethylene/α-olefin/diene terpolymer to the first polar polymer, and a second sulfonamide phthalic anhydride (SPA) linkage bonding the ethylene/α-olefin/diene terpolymer to the second polar polymer.

The present disclosure provides a process. In an embodiment a process is provided and includes first melt blending an ethylene/α-olefin/diene terpolymer and 4-azidosulfonylphthalic anhydride at a temperature greater than or equal to the decomposition temperature of the 4-azidosulfonylphthalic anhydride to form a sulfonamide phthalic anhydride grafted ethylene/α-olefin/diene terpolymer; and second melt blending the sulfonamide phthalic anhydride grafted ethylene/α-olefin/diene terpolymer and a polar polymer. The process further includes forming a sulfonamide phthalic anhydride (SPA) linkage between the ethylene/α-olefin/diene terpolymer and the polar polymer.

The present disclosure provides another process. In an embodiment, a process is provided and includes first melt blending an ethylene/α-olefin/diene terpolymer and 4-azidosulfonylphthalic anhydride at a temperature greater than or equal to the decomposition temperature of the 4-azidosulfonylphthalic anhydride to form a sulfonamide phthalic anhydride grafted ethylene/α-olefin/diene terpolymer; and second melt blending the sulfonamide phthalic anhydride grafted ethylene/α-olefin/diene terpolymer, a first polar polymer, and a second polar polymer that is different than the first polar polymer. The process further includes forming a first sulfonyl phthalic anhydride (SPA) linkage between the ethylene/α-olefin/diene terpolymer and the first polar polymer, and forming a second sulfonyl phthalic anhydride (SPA) linkage between the ethylene/α-olefin/diene terpolymer and the second polar polymer.

An advantage of the present disclosure is a sulfonamide phthalic anhydride linkage that bonds an ethylene/α-olefin/diene terpolymer to a polar polymer and avoids the processing drawbacks of free radical grafting chemistry.

Definitions

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The numerical ranges disclosed herein include all values from, and including, the lower value and the upper value. For ranges containing explicit values (e.g., 1 or 2, or 3 to 5, or 6, or 7) any subrange between any two explicit values is included (e.g., 1 to 2; 2 to 6; 5 to 7; 3 to 7; 5 to 6; etc.).

The term "alkyl" (or "alkyl group"), as described herein, refers to an organic radical derived from an aliphatic hydrocarbon by deleting one hydrogen atom therefrom. An alkyl group may be a linear, branched, cyclic or a combination thereof. The term "substituted alkyl," as used herein, refers to an alkyl, in which at least one hydrogen atom is substituted with a substituent that comprises at least one heteroatom. Heteroatoms include, but are not limited to, O, N, P and S. Substituents include, but are not limited to, halide, OR', NR'$_2$, PR'$_2$, P(=O)R'$_2$, SiR'$_3$; where each R' is independently a $C_1$-$C_{20}$ hydrocarbyl group.

The term "aryl" (or "aryl group"), as described herein, refers to an organic radical derived from aromatic hydrocarbon by deleting one hydrogen atom therefrom. An aryl group may be a monocyclic and/or fused ring system, each ring of which suitably contains from 5 to 7, preferably from 5 or 6 atoms. Structures wherein two or more aryl groups are combined through single bond(s) are also included. Specific examples include, but are not limited to, phenyl, tolyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl. The term "substituted aryl," as used herein, refers to an aryl, in which at least one hydrogen atom is substituted with a substituent comprising at least one heteroatom. Heteroatoms include, but are not limited to, O, N, P and S. Substituents include, but are not limited to, halide OR', NR'$_2$, PR'$_2$, P(=O)R'$_2$, SiR'$_3$; where each R' is independently a $C_1$-$C_{20}$ hydrocarbyl group.

The terms "blend" or "polymer blend," as used herein, refer to a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or," unless stated otherwise, refers to the listed members individually as well as in any combination.

The term, "ethylene/alpha-olefin polymer," as used herein, refers to an interpolymer that comprises a majority weight percent polymerized ethylene monomer (based on the total amount of polymerizable monomers), and at least one polymerized α-olefin.

The term, "ethylene-based polymer," as used herein, refers to a polymer that comprises a majority weight percent polymerized ethylene monomer (based on the total weight of polymerizable monomers), and optionally may comprise at least one polymerized comonomer.

The term "heteroatom" refers to an atom other than carbon or hydrogen. Nonlimiting examples of suitable heteroatoms include: F, Cl, Br, N, O, P, B, S, Si, Sb, Al, Sn, As, Se and Ge.

The terms, "hydrocarbyl" and "hydrocarbon" refer to substituents containing only hydrogen and carbon atoms, including branched or unbranched, saturated or unsaturated, cyclic, polycyclic or noncyclic species. Nonlimiting examples include alkyl-, cycloalkyl-, alkenyl-, alkadienyl-, cycloalkenyl-, cycloalkadienyl-, aryl-, and alkynyl-groups. The term "substituted hydrocarbon," as used herein, refers to a hydrocarbon in which at least one hydrogen atom is substituted with a substituent comprising at least one heteroatom. The term "unsubstituted hydrocarbyl" is a hydrocarbyl containing no heteroatoms.

The term "independently," or "each is independently selected from," or like terms refers to the separate selection of an element for each individual member within a target group. For example, the term "for each of Compound 1 through Compound 5, independently, $R_1$ through $R_5$ each independently is selected from methyl, ethyl, and propyl" indicates that (i) the property of a given substituent $R_1$-$R_5$ with respect to each Compound 1-5 is separate and individual (i.e., $R_1$ (methyl) of Compound 1 can be the same or different element as $R_1$ (methyl, ethyl, or propyl) for Compounds 2, 3, 4, or 5) and (ii) the selection for substituents $R_1$ through $R_5$ is separate for each individual substituent (i.e., $R_1$ (ethyl) can be the same or different element with respect to $R_2$, $R_3$, $R_4$, and $R_5$ (methyl, ethyl, or propyl).

The term, "interpolymer," or "terpolymer," as used herein, refers to polymers prepared by the polymerization of at least two different types of monomers. The generic term interpolymer thus includes copolymers, usually employed to refer to polymers prepared from two different monomers, and polymers prepared from more than two different types of monomers.

The term, "olefin-based polymer" (or "polyolefin" or "PO"), is a polymer containing, in polymerized form, a majority weight percent of an olefin, for example ethylene or propylene, based on the total weight of the polymer. Non-limiting examples of olefin-based polymers include ethylene-based polymers and propylene-based polymers. The term "olefin-based polymer" and "polyolefin" are used interchangeably.

A "polymer" is a macromolecular compound prepared by polymerizing monomers of the same or different type. "Polymer" includes homopolymers, copolymers, terpolymers, interpolymers, and so on. An "interpolymer" is a polymer prepared by the polymerization of at least two types of monomers or comonomers. It includes, but is not limited to, copolymers (which usually refers to polymers prepared from two different types of monomers or comonomers), terpolymers (which usually refers to polymers prepared from three different types of monomers or comonomers), tetrapolymers (which usually refers to polymers prepared from four different types of monomers or comonomers), and the like.

The term, "propylene/alpha-olefin polymer," as used herein, refers to an interpolymer that comprises a majority weight percent polymerized propylene monomer (based on the total amount of polymerizable monomers), and at least one polymerized α-olefin.

The term, "propylene-based polymer," as used herein, refers to a polymer that comprises a majority weight percent polymerized propylene monomer (based on the total amount of polymerizable monomers), and optionally may comprise at least one polymerized comonomer.

The term, "propylene/ethylene copolymer," as used herein, refers to an interpolymer that comprises a majority weight percent polymerized propylene monomer (based on the total amount of polymerizable monomers), polymerized ethylene monomer (second predominant monomer), and, optionally, at least polymerized one α-olefin.

DETAILED DESCRIPTION

The present disclosure provides a composition. In an embodiment, a composition is provided and includes an ethylene/α-olefin/diene terpolymer and a polar polymer. The composition includes a sulfonamide phthalic anhydride (SPA) linkage bonding the ethylene/α-olefin/diene terpolymer to the polar polymer.

1. Ethylene/α-Olefin/Diene Terpolymer

The present composition includes an ethylene/α-olefin/diene terpolymer. The term "ethylene/α-olefin/diene terpolymer," as used herein, is a polymer with a majority weight percent (i.e., greater than 50 wt %) of units derived from ethylene, and also includes units derived from α-olefin comonomer, and units derived from a diene comonomer.

The α-olefin comonomer is selected from $C_3$-$C_{12}$ α-olefin, or $C_3$-$C_8$ α-olefin. In an embodiment, the α-olefin comonomer is selected from propylene, butene, and octene.

In an embodiment, the α-olefin is propylene comonomer and the ethylene/α-olefin/diene terpolymer is an ethylene/ propylene/diene terpolymer. An "ethylene/propylene/diene polymer," or "EPDM," is as a polymer with a majority amount (greater than 50 wt %) of units derived from ethylene, and also includes units derived from propylene comonomer, and units derived from a diene comonomer.

The ethylene/α-olefin/diene terpolymer includes units derived from a diene monomer. The diene can be conjugated-, non-conjugated-, straight chain-, branched chain- or cyclic-hydrocarbon diene having from 6 to 15 carbon atoms. Nonlimiting examples of suitable diene include 1,4-hexadiene; 1,6-octadiene; 1,7-octadiene; 1,9-decadiene; branched chain acyclic diene, such as 5-methyl-1,4-hexadiene, 3,7-dimethyl-1,6-octadiene, 3,7-dimethyl-1,7-octadiene and mixed isomers of dihydromyricene and dihydroocinene; single ring alicyclic dienes, such as 1,3-cyclopentadiene, 1,4-cyclohexadiene, 1,5-cyclooctadiene and 1,5-cyclododecadiene; and multi-ring alicyclic fused and bridged ring dienes, such as tetrahydroindene, methyl tetrahydroindene, dicyclopentadiene, and bicyclo-(2,2,1)-hepta-2,5-diene; alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene, norbornadiene, 5-ethylidene-2-norbornene (ENB), 5-vinylidene-2-norbornene (VNB), 5-methylene-2-norbornene (MNB), dicyclopentadiene (DCPD); and combinations thereof.

Further nonlimiting examples of suitable diene include 4-methyl-1,4-hexadiene, 7-methyl-1,6-octadiene, 5,7-dimethyl-1,6-octadiene, 3,7,11-trimethyl-1,6,10-octatriene, 6-methyl-1,5-heptadiene, 1,3-butadiene, 1,6-heptadiene, 1,8-nonadiene, 1,9-decadiene, 1,10-undecadiene, 1,5-cyclododecadiene, bicyclo[2.2.1]hepta-2,5-diene (norbornadiene), tetracyclododecene, butadiene, dicyclopentadiene, vinyl norbornene, mixed isomers of dihydromyricene and dihydroocinene, tetrahydroindene, methyl tetrahydroindene, 5-propenyl-2-norbornene, 5-isopropylidene-2-norbornene, 5-(4-cyclopentenyl)-2-norbornene, 5-cyclohexylidene-2-norbornene, 5-vinyl-2-norbornene, and combinations thereof.

In an embodiment, the diene is selected from VNB and ENB.

In an embodiment, the diene is ENB.

In an embodiment, the EPDM includes:
(i) from at least 60 wt %, or 65 wt %, or 70 wt % to 75 wt %, or 80, or 85 wt % units derived from ethylene;
(ii) from 15 wt %, or 20 wt % to 25 wt %, or 30 wt % units derived from propylene; and
(iii) from 0.1 wt %, or 0.3 wt %, or 0.5 wt % to 1.0 wt %, or 5 wt %, or 10 wt % units derived from ENB. Weight percent is based on the total weight of the EPDM.

In an embodiment, the EPDM has a Mooney viscosity from 20, or 25, or 30, or 40, or 50, or 60 to 70, or 80, or 90, or 100, or 200, or 300 Mooney units (MU).

In an embodiment, the EPDM is provided in a composition containing the EPDM and an oil.

2. Polar Component

The present composition includes a polar component. A "polar component," as used herein, is a material that contains a heteroatom (i.e., an atom other than carbon (C) or hydrogen (H)). In an embodiment, the heteroatom of the polar component is oxygen (O) and/or nitrogen (N). The heteroatom may be in the state of a reactive proton, such as —OH or —NH.

Nonlimiting examples of suitable polar components include metal (such as metal foil), cellulosic material (such as paper), and polar polymer.

In an embodiment, the polar component is a polar polymer. Nonlimiting examples of suitable polar polymer include polyamide (nylon), ethylene/vinyl alcohol (EVOH) copolymer, polyurethane, polyacrylate, polyacrylonitrile, polycarbonate, polybutylene terephthalate (PBT), polyethylene terephthalate (PET), and combinations thereof.

In an embodiment, the polar polymer is nylon.

3. Sulfonamide Phthalic Anhydride Linkage (SPA)

The present composition includes a sulfonamide phthalic anhydride (SPA) linkage. The SPA linkage bonds (covalently bonds) the ethylene/α-olefin/diene terpolymer to the polar component. The SPA is formed from a sulfonyl azide derivative (SD) with the Structure (1) below.

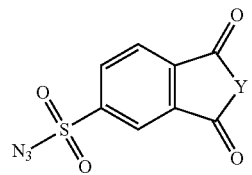

Structure (1)

For Structure (1), Y is selected from O, S, PH, PR, NH, and NR. When Y is NR or PR, R is selected from an alkyl group and an aryl group.

In an embodiment, the aromatic moiety of Structure (1) may include substituents as shown in Structure (1a) below.

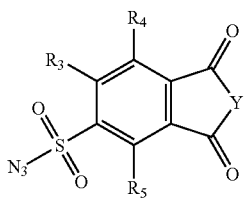

Structure (1a)

wherein Y is selected from O, S, PH, NH, $PR_1$ and $NR_2$; $R_1$, $R_2$, $R_3$, $R_4$ and $R_5$ each independently is selected from an unsubstituted hydrocarbyl and a substituted hydrocarbyl. Optionally, $R_3$ and $R_4$ can be linked together to form ring structures with such ring structures containing from 4 to 50 carbon atoms.

The SD is grafted to the ethylene/α-olefin/diene terpolymer by admixing the sulfonyl azide derivative with the ethylene/α-olefin/diene terpolymer and heating the admixture to at least the decomposition temperature of the sulfonyl azide derivative. The decomposition temperature is the temperature at which the sulfonyl azide derivative converts to the sulfonyl nitrene, eliminating nitrogen and heat in the process. In an embodiment, the ethylene/α-olefin/diene terpolymer and the sulfonyl azide derivative are dry blended to form a uniform mixture and this mixture is subsequently added to melt processing equipment, e.g., a melt extruder to achieve the grafting reaction, at a temperature that is at least the decomposition temperature of the sulfonyl azide derivative. The term "melt processing" (or "melt processing conditions") is a process in which the ethylene/α-olefin/diene terpolymer is softened or melted. Nonlimiting examples of suitable melt processing procedures include extrusion (including co-extrusion), pelletizing, film blowing, film casting, thermoforming, and compounding in polymer melt form. "Melt blending" is a type of melt processing whereby (i) the ethylene/α-olefin/diene terpolymer or the sulfonamide phthalic anhydride grafted ethylene/α-olefin/diene terpolymer and (ii) at least one other (i.e., different) component are combined or otherwise mixed together, and at least one of the components is in a melted state. The melt blending may be accomplished by way of batch mixing, extrusion blending, extrusion molding, and any combination thereof.

Bounded by no particular theory, it is believed that under melt processing conditions, the sulfonyl azide derivative decomposes to form an intermediate singlet sulfonyl nitrene and nitrogen gas. The reactive singlet sulfonyl nitrene undergoes carbon-hydrogen bond insertion to form secondary sulfonamide linkages (i) to the ethylene/α-olefin/diene terpolymer backbone, and/or (ii) to moieties pendent to the terpolymer backbone. Nitrene insertion yields one or more —N—C— covalent bonds between the sulfonamide derivative and the ethylene/α-olefin/diene terpolymer. A nonlimiting example of an —N—C— covalent bond between the sulfonamide derivative and the ethylene/α-olefin/diene terpolymer (or "SD-g-terpolymer") is shown in Structure (2) below.

Structure (2)

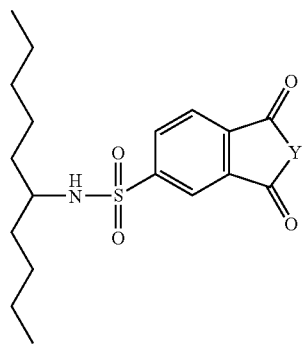

Y of Structure (2) is selected from O, S, PH, PR, NH, and NR. When Y is NR or PR, R is selected from an alkyl group and an aryl group. The chain shown in Structure (2) is a generic representation of the polymer backbone of the ethylene/α-olefin/diene terpolymer. It is understood that nitrene insertion and the resultant —N—C— bonds can be formed on moieties pendent to the backbone of the ethylene/α-olefin/diene terpolymer.

In an embodiment, the sulfonyl azide derivative is 4-azidosulfonylphthalic anhydride (ASPA). The ASPA has the Structure (3) provided below.

Structure (3)

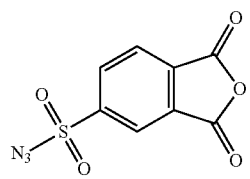

Under melt processing conditions, the ASPA decomposes to form an intermediate singlet sulfonyl nitrene and nitrogen gas. The reactive singlet sulfonyl nitrene undergoes carbon-hydrogen bond insertion to form secondary sulfonamide linkages (i) to the ethylene/α-olefin/diene terpolymer backbone, and/or (ii) to moieties pendent to the terpolymer backbone, thereby producing a sulfonamide phthalic anhydride-grafted-polyolefin or "SPA-g-terpolymer" with the Structure (4) below. The chain shown in Structure (4) is a generic representation of the polymer backbone of the ethylene/α-olefin/diene terpolymer.

Structure (4)

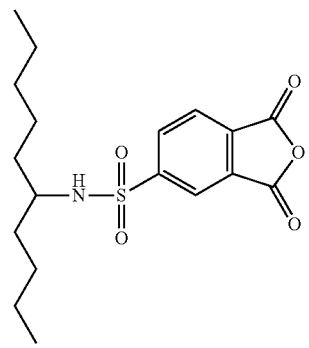

When the ASPA is grafted to the ethylene/α-olefin/diene terpolymer, a sulfonamide phthalic anhydride grafted ethylene/α-olefin/diene terpolymer (or "SPA-g-terpolymer") is formed. Applicant discovered the ASPA grafting reaction occurs with little, or no, crosslinking, and little molecular weight degradation by chain scission when propylene comonomer is present in the ethylene/α-olefin/diene terpolymer.

In an embodiment, the ethylene/α-olefin/diene terpolymer is ethylene/propylene/ENB terpolymer (EPDM1). Nonlimiting examples of covalent —N—C— bonds between the SPA and EPDM1 include the following Structures (5)-(9):

Structure (5) (—N—C— bond, where C is a tertiary carbon in the pendent ENB):

Structure (5)

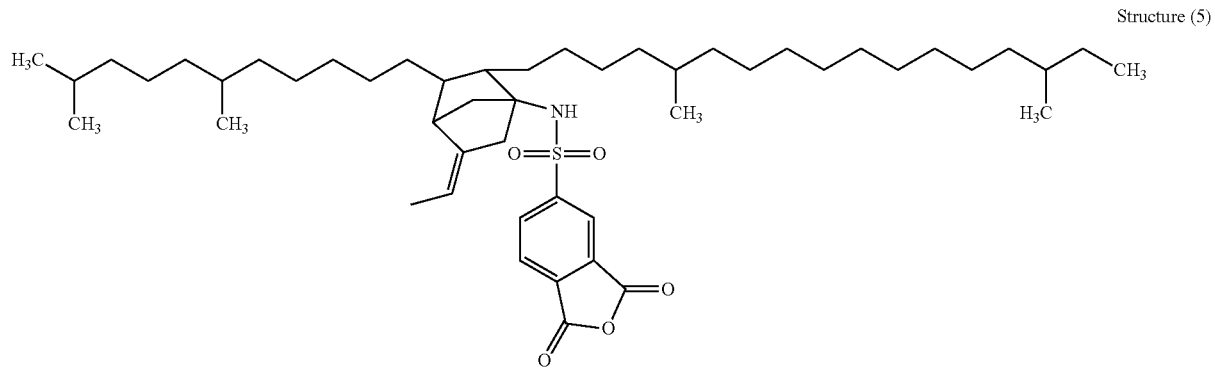 [SMILES: C/C=C1/CC2(NS(=O)(=O)c3ccc4c(c3)C(=O)OC4=O)CC1C(CCCCCC(C)CCCC(C)C)C2CCCCC(C)CCCCCCCCCC(C)CC]

Structure (6) (—N—C— bond, where C is a primary carbon in the pendent ENB):
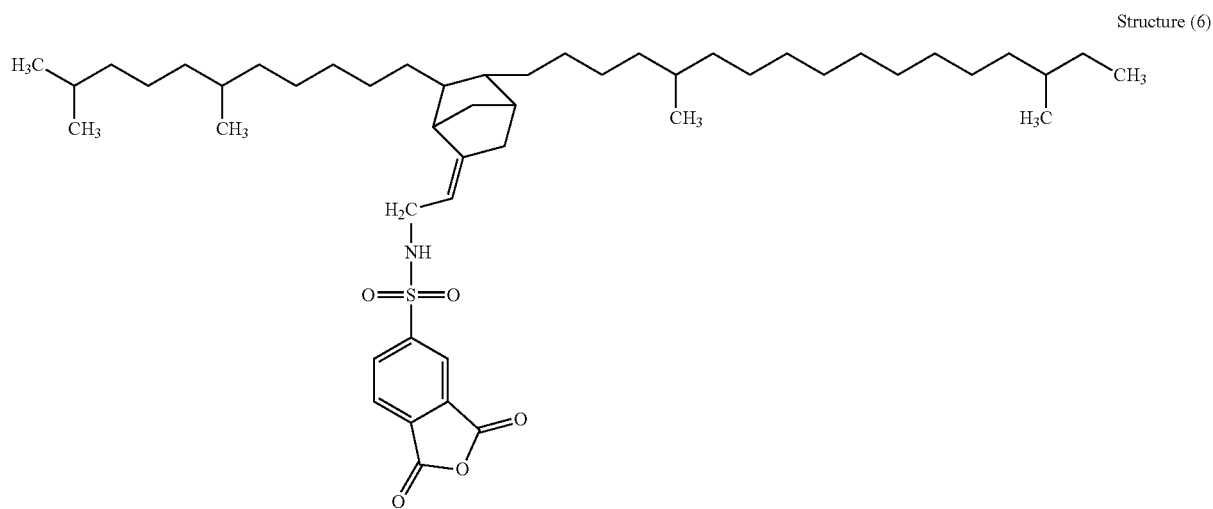 [SMILES: CCC(C)CCCCCCCCCC(C)CCCCC1C2C/C(=C/CNS(=O)(=O)c3ccc4c(c3)C(=O)OC4=O)C(C2)C1CCCCCC(C)CCCC(C)C]
Structure (7) (sulfonamide aziridine bond):
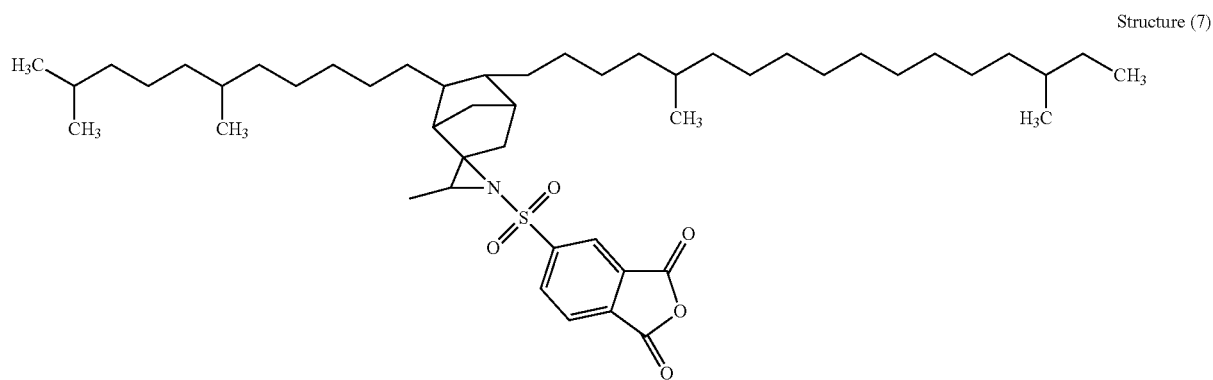 [SMILES: CCC(C)CCCCCCCCCC(C)CCCCC1C2CC(C1CCCCCC(C)CCCC(C)C)C1(C2)C(C)N1S(=O)(=O)c1ccc2c(c1)C(=O)OC2=O]
Structure (8) (—N—C— bond, where C is a secondary carbon in the pendent ENB):
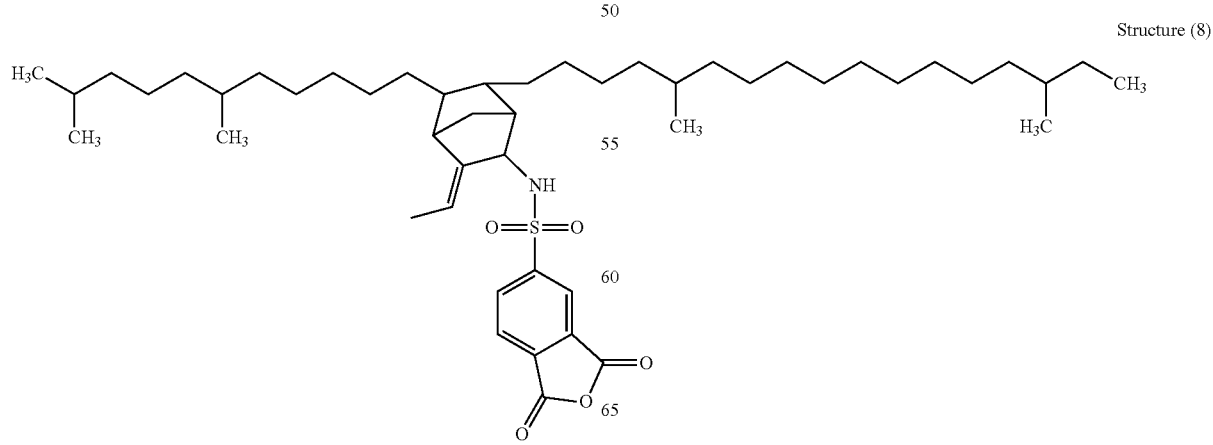

Structure (9) (—N—C— bond to an ethylene triad in EPDM1, where C is a secondary carbon in the backbone of EPDM1):

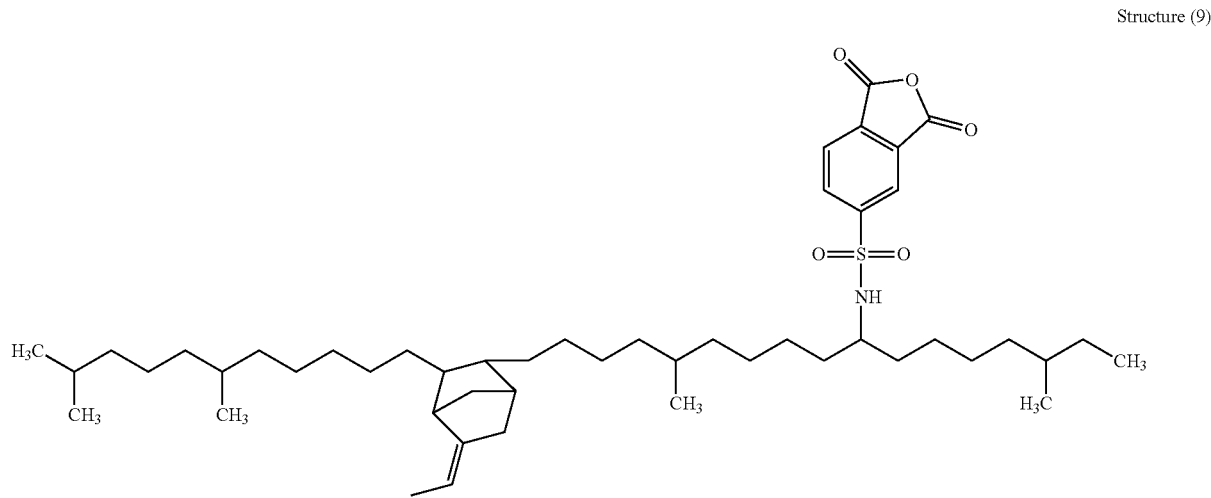 [SMILES: C/C=C1/CC2CC1C(CCCCCC(C)CCCC(C)C)C2CCCCC(C)CCCCC(CCCCC(C)CC)NS(=O)(=O)c1ccc2c(c1)C(=O)OC2=O]

In an embodiment, the ethylene/α-olefin/diene terpolymer is ethylene/propylene/ENB terpolymer (EPDM1) and the 4-azidosulfonylphthalic anhydride decomposes to give sulfonyl nitrenes, which undergo grafting onto the EPDM1 polymer by addition across carbon-carbon double bonds, thereby producing a sulfonamide phthalic anhydride-grafted-polyolefin or "SPA-g-terpolymer" that is a sulfonamide aziridine phthalic anhydride-grafted-polyolefin with the Structure (7) above.

In an embodiment, EPDM1 and the ASPA are admixed under melt processing conditions to produce a sulfonamide phthalic anhydride grafted ethylene-based polymer (SPA-g-EPDM1) with a grafting efficiency (GE) from at least 50%, or 60%, or 70%, or 80% to 90%, or 95%, or 99%. In a further embodiment, the SPA-g-EPDM1 contains maleic anhydride in an amount from 0.1 wt %, or 0.2 wt %, or 0.3 wt %, or 0.4 wt %, or 0.5 wt %, or 0.6 wt % to 0.7 wt %, or 0.8 wt %, or 0.9 wt %, or 1.0 wt %, or 1.1 wt %, or 1.5 wt %, or 2.0 wt %, or 3 wt %, or 5 wt %, or 10 wt %. Weight percent maleic anhydride is based on the total weight of the SPA-g-EPDM1.

In an embodiment, EPDM1, the ASPA, and an antioxidant are admixed under melt processing conditions to produce a sulfonamide phthalic anhydride grafted ethylene-based polymer (SPA-g-EPDM1) with a grafting efficiency (GE) from at least 50%, or 60%, or 70%, or 80% to 90%, or 95%, or 99%. In a further embodiment, the SPA-g-EPDM1 contains maleic anhydride in an amount from 0.1 wt %, or 0.2 wt %, or 0.3 wt %, or 0.4 wt %, or 0.5 wt %, or 0.6 wt % to 0.7 wt %, or 0.8 wt %, or 0.9 wt %, or 1.0 wt %, or 1.1 wt %, or 1.5 wt %, or 2.0 wt %, or 3 wt %, or 5 wt %, or 10 wt %. Weight percent maleic anhydride is based on the total weight of the SPA-g-EPDM1. In an embodiment, EPDM1 and the ASPA are admixed with from greater than 0 wt %, or 0.01 wt %, or 0.02 wt % to 0.03 wt %, or 0.04 wt %, or 0.05 wt %, or 0.10 wt % antioxidant, based on the total weight of EPDM1, ASPA, and antioxidant present in the admixture. A nonlimiting example of a suitable antioxidant is pentaerythritol tetrakis(3-(3,5-di-tert-butyl-4-hydroxyphenyl)propionate), commercially available as IRGANOX™ 1010 from Ciba Specialty Chemicals.

In an embodiment, the SD-g-terpolymer is subsequently melt blended with a polar polymer. Under melt processing conditions, the SD bonds to (i) the terpolymer and (ii) bonds to the polar polymer and forms at least one SPA linkage between the terpolymer and the polar component. The "SPA linkage" has the Structure (10) below.

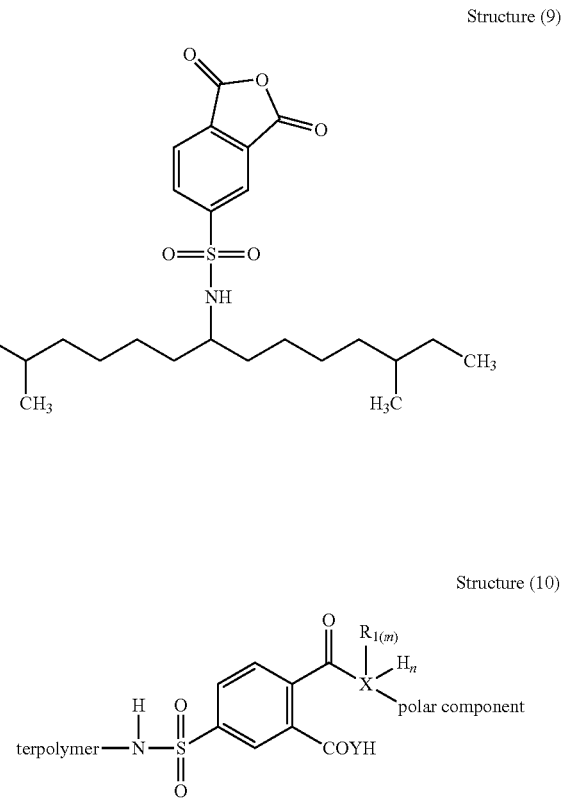

wherein the nitrogen, N, is bound to a carbon, C, of the terpolymer;
X is selected from O, P, S, and N;
Y is selected from O, S, PH, PR, NH, and NR and R is selected from an alkyl group and an aryl group;
$R_1$ is a $C_1$-$C_8$ alkyl group;
m and n each independently is 0 or 1 with the proviso when m=1, n=0 and when n=1, m=0. In other words, Structure (10) contains $R_m$ or $H_n$.

The "terpolymer" in Structure (10) is the ethylene/α-olefin/diene terpolymer. In an embodiment, Y of Structure (10) is oxygen, or O.

In an embodiment, Y of Structure (10) is oxygen, O; X of Structure (10) is nitrogen, N; and m=0; and n=1.

In an embodiment, the ethylene/α-olefin/diene terpolymer is EPDM1 and the composition includes EPDM1-SPA-polar component with SPA linkage as shown in Structure (11) below.

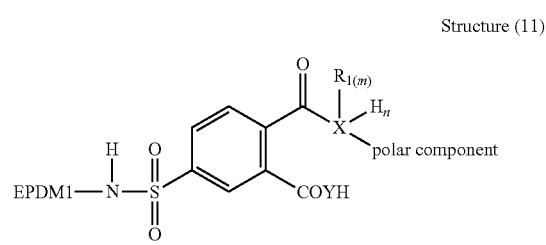

wherein the nitrogen, N, is bound to a carbon, C, of EPDM1;

X is selected from O, P, S, and N;
Y is selected from O, S, PH, PR, NH, and NR and R is selected from an alkyl group and an aryl group;
$R_1$ is a $C_1$-$C_8$ alkyl group;
m and n each independently is 0 or 1 with the proviso when m=1, n=0 and when n=1, m=0. In other words, Structure (11) contains $R_m$ or $H_n$.

The bond between the nitrogen atom, N, and the EPDM1 is a —N—C— bond.

In an embodiment, Y of Structure (11) is oxygen, or O.

In an embodiment, Y of Structure (11) is oxygen, O; X of Structure (11) is nitrogen, N; and m=0; and n=1.

In an embodiment, the ethylene/α-olefin/diene terpolymer is EPDM1 with the SPA linkage to the polar component as shown in Structure (11). The polar component is a polyamide (denoted as N-PA6), a polar polymer. Melt blending the SPA-g-EPDM1 with the polyamide bonds the EPDM1 with the polyamide by way of an SPA linkage (EPDM-SPA-polyamide) that includes an imide bond Structure (12b) in Scheme 1 below.

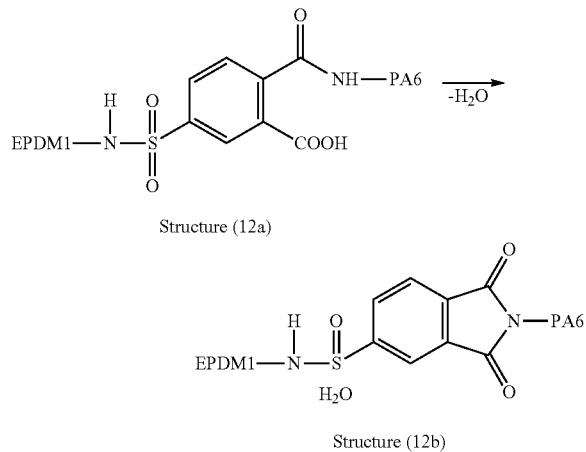

Scheme (1)

Structure (12a)

Structure (12b)

In an embodiment, any of Structures (2)-(12b) can include the substituents presented in Structure (1a).

The present disclosure provides another composition. In an embodiment, a composition is provided and includes an ethylene/α-olefin/diene terpolymer, a first polar polymer, and a second polar polymer different than the first polar polymer. The composition also includes (i) a first sulfonamide phthalic anhydride (SPA) linkage bonding the ethylene/α-olefin/diene terpolymer to the first polar polymer and (ii) a second SPA linkage bonding the ethylene/α-olefin/diene terpolymer to the second polar polymer.

The SPA linkage is present (i) between the ethylene/α-olefin/diene terpolymer and the first polar polymer (first linkage) and (ii) another SPA linkage is present between the ethylene/α-olefin/diene terpolymer and the second polar polymer (second linkage). The first polar polymer can be any polar polymer as disclosed above. The second polar polymer can be any polar polymer as disclosed above with the proviso that the second polar polymer is different than the first polar polymer.

The SPA linkage is the SPA linkage as disclosed above as in Structure (10) or Structure (11) for example.

In an embodiment, the ethylene/α-olefin/diene terpolymer is an ethylene/propylene/diene terpolymer (EPDM). The composition includes the following SPA linkages (i) EPDM-SPA-polar polymer 1 and (ii) EPDM-SPA-polar polymer 2. The composition may optionally include the SPA linkage between the first polar polymer and the second polar polymer such that the composition also includes the linkage:

polar polymer 1-SPA-polar polymer 2.

Without wishing to be bound by any particular theory, Applicant believes the present composition will advantageously exhibit improved impact performance, such as a higher IZOD impact strength, compared to blends of ethylene/α-olefin/diene terpolymer and polar polymer that lack a SPA linkage.

The present composition may comprise one or more embodiments disclosed herein.

4. Process

The present disclosure provides a process. In an embodiment, the process includes first melt blending an ethylene/α-olefin/diene terpolymer and 4-azidosulfonylphthalic anhydride, and optional antioxidant at a temperature greater than or equal to the decomposition temperature of the 4-azidosulfonylphthalic anhydride to form a sulfonamide phthalic anhydride grafted ethylene/α-olefin/diene terpolymer (SPA-g-terpolymer). The process includes second melt blending the sulfonamide phthalic anhydride grafted ethylene/α-olefin/diene terpolymer (SPA-g-terpolymer) and a polar polymer, and optional antioxidant. The process includes forming a sulfonyl phthalic anhydride (SPA) linkage between the ethylene/α-olefin/diene terpolymer and the polar polymer.

The ethylene/α-olefin/diene terpolymer, 4-azidosulfonylphthalic anhydride, antioxidant, and polar polymer may be any respective ethylene/α-olefin/diene terpolymer, 4-azidosulfonylphthalic anhydride, antioxidant, and polar polymer previously disclosed herein.

As used herein, "first melt blending" and "second melt blending" refer to sequential melt blending steps, wherein the "first melt blending" step occurs prior to, or before, the "second melt blending" step. All, or substantially all, first melt blending is completed by forming SPA-g-terpolymer before second melt blending commences. Second melt blending commences with the addition of polar polymer to the SPA-g-terpolymer. While some SPA-g-terpolymer may form after second melt blending begins (due to the presence of residual free ethylene/α-olefin/diene terpolymer and/or residual free 4-azidosulfonylphthalic anhydride), it is understood that all, or substantially all, of the SPA-g-terpolymer is formed by first melt blending before (i.e., prior to) the start of second melt blending.

In an embodiment, the first melt blending and the second melt blending are not simultaneous (i.e., they do not occur at the same time).

The first melt blending and the second melt blending steps may occur in the same melt processing equipment (such as an extruder), or in separate melt processing equipment. Nonlimiting examples of suitable melt blending procedures include extrusion (including co-extrusion), pelletizing, film blowing, film casting, thermoforming, and compounding in polymer melt form. The first melt blending and the second melt blending may occur in a continuous process or a batch process.

A "continuous process," as used herein, refers to a melt blending process in which first melt blending and second melt blending occur in the same melt processing equipment, without removing the intermediate product (SPA-g-terpolymer) from the melt processing equipment. For example, during a continuous process, the ethylene/α-olefin/diene terpolymer and 4-azidosulfonylphthalic anhydride are first melt blended to form the SPA-g-terpolymer in an extruder, and then the polar polymer is added to the same extruder and the SPA-g-terpolymer and polar polymer are second melt blended to form the sulfonyl phthalic anhydride (SPA) linkage between the ethylene/α-olefin/diene terpolymer and the polar polymer.

A "batch process," as used herein, refers to a melt blending process in which the intermediate product (SPA-g-terpolymer) is removed from the melt processing equipment after completing first melt blending and before commencing second melt blending. For example, during a batch process, (i) a first batch containing the ethylene/α-olefin/diene terpolymer and 4-azidosulfonylphthalic anhydride are first melt blended to form the SPA-g-terpolymer in a first extruder; (ii) the SPA-g-terpolymer is removed from the first extruder; and then (iii) a second batch containing the SPA-g-terpolymer and the polar polymer are second melt blended to form the sulfonyl phthalic anhydride (SPA) linkage between the ethylene/α-olefin/diene terpolymer and the polar polymer in a second extruder, wherein the first extruder may be the same or different than the second extruder. When the SPA-g-terpolymer is removed from the extruder after the first melt blending step, it may or may not be formed into pellets prior to commencing the second melt blending step.

The process includes first melt blending the ethylene/α-olefin/diene terpolymer and 4-azidosulfonylphthalic anhydride, and optional antioxidant at a temperature greater than or equal to the decomposition temperature of the 4-azidosulfonylphthalic anhydride to form a sulfonamide phthalic anhydride grafted ethylene/α-olefin/diene terpolymer (or SPA-g-terpolymer). The 4-azidosulfonylphthalic anhydride undergoes decomposition during the first melt blending to trigger the nitrene insertion reaction into (i) one or more carbon-hydrogen bonds of the ethylene/α-olefin/diene terpolymer, and/or (ii) one or more carbon-carbon double bonds present in the diene of the ethylene/α-olefin/diene terpolymer (yielding a sulfonamide aziridine), as previously disclosed herein. In an embodiment, first melt blending forms a SPA-g-terpolymer of any of Structures (4)-(9), or of any of Structures (4), (5), (6), (8), and (9), as previously disclosed herein. In another embodiment, first melt blending forms a sulfonamide aziridine phthalic anhydride grafted terpolymer of Structure (7), as previously disclosed herein. In a further embodiment, first melt blending includes grafting the 4-azidosulfonylphthalic anhydride to the ethylene/α-olefin/diene terpolymer with at least 50% grafting efficiency and forming the SPA-g-terpolymer. Applicant discovered the first melt blending grafting reaction occurs with little, or no, crosslinking, and little molecular weight degradation by chain scission when propylene comonomer is present in the ethylene/α-olefin/diene terpolymer.

In an embodiment, first melt blending occurs in the absence of polar polymer. Thus, in an embodiment, first melt blending excludes polar polymer.

In an embodiment, the ethylene/α-olefin/diene terpolymer and the 4-azidosulfonylphthalic anhydride are dry blended to form a uniform mixture and this mixture is subsequently first melt blended to form the SPA-g-terpolymer.

The process includes second melt blending the SPA-g-terpolymer and a polar polymer, and optional antioxidant. In an embodiment, second melt blending occurs at a temperature greater than or equal to the crystalline melting temperature (Tc) of the polar polymer, or at a temperature greater than or equal to the glass transition temperature (Tg) of the polar polymer. During the second melt blending, the heteroatom of the polar polymer bonds with the anhydride moiety of the SPA as previously disclosed herein to form an ester linkage. Thus, the polar polymer is second melt blended with the SPA-g-terpolymer to form the SPA linkage between the ethylene/α-olefin/diene terpolymer and the polar polymer. In an embodiment, second melt blending forms a SPA linkage of any of Structures (10)-(12b), as previously disclosed herein.

In an embodiment, the ethylene/α-olefin/diene terpolymer is an EPDM.

In an embodiment, the process includes forming a composition containing the ethylene/α-olefin/diene terpolymer; the polar component; and the sulfonamide phthalic anhydride linkage (SPA) bonding the ethylene/α-olefin/diene terpolymer to the polar component. The composition may be any composition previously disclosed herein.

The present disclosure provides another process. In an embodiment, the process includes first melt blending an ethylene/α-olefin/diene terpolymer and 4-azidosulfonylphthalic anhydride, and optional antioxidant, at a temperature greater than or equal to the decomposition temperature of the 4-azidosulfonylphthalic anhydride to form a sulfonamide phthalic anhydride grafted ethylene/α-olefin/diene terpolymer (or "SPA-g-terpolymer"). The process includes second melt blending the SPA-g-terpolymer, a first polar polymer, and a second polar polymer (the second polar polymer being different than the first polar polymer), and optional antioxidant. The process includes forming a first sulfonyl phthalic anhydride (SPA) linkage between the ethylene/α-olefin/diene terpolymer and the first polar polymer, and forming a second sulfonyl phthalic anhydride (SPA) linkage between the ethylene/α-olefin/diene terpolymer and the second polar polymer.

The ethylene/α-olefin/diene terpolymer, 4-azidosulfonylphthalic anhydride, antioxidant, first polar polymer, and second polar polymer may be any respective ethylene/α-olefin/diene terpolymer, 4-azidosulfonylphthalic anhydride, antioxidant, and polar polymer, previously disclosed herein, with the proviso that the second polar polymer is different than the first polar polymer. The first melt blending and second melt blending may be any melt blending previously disclosed herein, such as in a continuous process or a batch process.

In an embodiment, the process includes forming a composition containing (i) a first sulfonamide phthalic anhydride (SPA) linkage bonding the ethylene/α-olefin/diene terpolymer to the first polar polymer and (ii) forming a second sulfonamide phthalic anhydride (SPA) linkage bonding the ethylene/α-olefin/diene terpolymer to the second polar polymer. In an embodiment, the process includes forming a composition containing the ethylene/α-olefin/diene terpolymer; the first polar polymer; the second polar polymer; the first SPA linkage bonding the ethylene/α-olefin/diene terpolymer to the first polar polymer; and the second SPA linkage bonding the ethylene/α-olefin/diene terpolymer to the second polar polymer.

In an embodiment, the ethylene/α-olefin/diene terpolymer is an ethylene/propylene/diene terpolymer (EPDM) and the process includes forming the following SPA linkages: (i) EPDM-SPA-polar polymer 1 and (ii) EPDM-SPA-polar polymer 2. In an embodiment, the process also includes forming a SPA linkage between the first polar polymer and the second polar polymer such that a composition is formed that also includes the linkage:

polar polymer 1-SPA-polar polymer 2.

The present processes may comprise one or more embodiments disclosed herein.

The present compositions may be used as a tie layer between extruded sheets, films or profiles; for fibers or dispersions; in automotive skins; awnings; tarps; roofing construction (for example, adhesives to epoxy, urethane or acrylic-based substrates for all roofing applications, such as insulation bonding, liquid roofing, facade sealant, expansion joints, wet-room sealants, pitched roof, acrylics-adhered roof, bitumen bonding, and PUR-adhered refurbishment); paintable automotive skins and steering wheels; paintable injection molded toys; powder coatings; powder slush moldings or rotational cast moldings; consumer durables; grips; computer components; belts; adhesives; fabrics; carpets; artificial turf; coatings; wire and cable; raincoats and similar protective apparel; and any combination of the foregoing. Additional applications are described herein.

The present compositions may be used for novel compounds for footwear; automotive; consumer durables; appliances; electronic housing; apparel; and conveyor belts. The present compositions may also be used as impact modifier for nylon.

By way of example, and not limitation, examples of the present disclosure are provided.

EXAMPLES

1. Test Methods

Density is determined in accordance with American Society for Testing and Materials (ASTM) procedure ASTM D792-00, Method B.

Melt flow (MF) (I2) in g/10 min for propylene-based polymers and ethylene-based polymers is measured using ASTM D-1238-04 condition 190° C./2.16 kg. Melt flow (MF) (I10) in g/10 min for propylene-based polymers and ethylene-based polymers is measured using ASTM D-1238-04, Condition 190° C./10.0 kg.

Mooney viscosity ("MV")—Interpolymer MV (ML1+4 at 125° C.) is measured in accordance with ASTM 1646-04, with a one minute preheat time and a four minute rotor operation time. The instrument is an Alpha Technologies Rheometer MDR 2000. For dual reactor polymerizations in series, the Mooney viscosity of the second reactor component is determined by the following equation: log ML=n(A) log ML(A)+n(B) log ML(B); where ML is the Mooney viscosity of the final reactor product, ML(A) is the Mooney viscosity of the first reactor polymer, ML(B) is the Mooney viscosity of the second reactor polymer, n(A) is the weight fraction of the first reactor polymer, and n(B) is the weight fraction of the second reactor polymer. Each measured Mooney viscosity is measured as discussed above. The weight fraction of the second reactor polymer is determined as follows: n(B)=1−n(A), where n(A) is determined by the known mass of first polymer transferred to the second reactor.

The predicted half-life of the 4-azidosulfonylphthalic anhydride is measured using DSC by scanning the 4-azidosulfonylphthalic anhydride at various heating rates. The DSC data collected is utilized to compute the kinetic parameters using AKTS-Thermokinetics Software (available from Advanced Kinetics and Technology Solutions AG). Applying the computed kinetic parameters, the reaction progress for a specific temperature profile is predicted. Subsequently, the predicted half-life of the 4-azidosulfonylphthalic anhydride molecule is obtained from the reaction progress vs. time plot at a given temperature. The same procedure is utilized for a blend of 4-azidosulfonylphthalic anhydride in ENGAGE™ EG8400 (an ethylene/octene copolymer available from The Dow Chemical Company) at a concentration of 1.96 wt % of 4-azidosulfonylphthalic anhydride. The predicted half-life is measured in seconds (sec.).

Limiting impact energy is determined using the German Federal Institute for Testing Materials (BAM) Fall Hammer Test. Impact energy is imparted to a 40 mm³ sample of 4-azidosulfonylphthalic anhydride by a falling weight using the BAM Fall Hammer apparatus. The limiting impact energy is determined as the lowest energy at which a flash, flame or explosion is observed. The test assesses the sensitivity of the 4-azidosulfonylphthalic anhydride to drop-weight impact. The method yields quantitative results in the form of limiting impact energy. The testing is carried out at Chilworth Technology Inc., now part of DEKRA Insight. The limiting impact energy is measured in Joules (J).

Flash point is measured in accordance with ASTM D 3278.

Differential Scanning Calorimetry (DSC)

Differential Scanning Calorimetry (DSC) is used to measure crystallinity in the polymer (e.g., ethylene-based (PE) polymers, or propylene-based (PP) polymers). About 5 to 8 mg of polymer sample is weighed and placed in a DSC pan. The lid is crimped on the pan to ensure a closed atmosphere. The sample pan is placed in a DSC cell, and then heated, at a rate of approximately 10° C./min, to a temperature of 180° C. for PE (230° C. for polypropylene). The sample is kept at this temperature for three minutes. Then the sample is cooled at a rate of 10° C./min to −60° C. for PE (−40° C. for PP), and kept isothermally at that temperature for three minutes. The sample is next heated at a rate of 10° C./min, until complete melting (second heat). The percent crystallinity is calculated by dividing the heat of fusion ($H_f$), determined from the second heat curve, by a theoretical heat of fusion of 292 J/g for PE (165 J/g, for PP), and multiplying this quantity by 100 (for example, % cryst.=($H_f$/292 J/g)× 100 (for PE)).

Unless otherwise stated, melting point(s) ($T_m$) of each polymer is determined from the second heat curve (peak Tm), and the crystallization temperature ($T_c$) is determined from the first cooling curve (peak Tc).

Glass transition temperature (Tg) is determined from the DSC heating curve where half the sample has gained the liquid heat capacity, as described in Bernhard Wunderlich, *The Basis of Thermal Analysis, in Thermal Characterization of Polymeric Materials* 92, 278-279 (Edith A. Turi ed., 2d ed. 1997). Baselines are drawn from below and above the glass transition region and extrapolated through the Tg region. The temperature at which the sample heat capacity is half-way between these baselines is the Tg.

¹H NMR

Samples are prepared by weighing 5 to 30 mg of the sample and dissolving it in a suitable deuterated nuclear magnetic resonance (NMR) solvent at room temperature (23° C.). The deuterated NMR solvents used are methylene chloride-$d_2$, chloroform (CDCl$_3$), and acetone (acetone-$d_6$), as shown in the experimental results detailed below. The NMR tubes utilized are from Norell (No. 502). The data is collected using a Varian Mercury Vx 400 MHz spectrometer or a VNMRS 500 MHz spectrometer. The VNMRS 500 MHz spectrometer has a pulse field gradient probe (PFG). The ¹H NMR spectra is collected at a temperature of 30° C., as shown in the experimental results detailed below. The data is collected with 16 scans.

¹³C NMR

The data is collected using a Varian Mercury 400 MHz spectrometer, corresponding to a ¹³C resonance frequency of 101 MHz, or a VNMR-500 spectrometer corresponding to a ¹³C resonance frequency of 126 MHz at a temperature of 30° C., as shown in the experimental results detailed below.

2. Example Synthesis of 4-Azidosulfonylphthalic Anhydride (ASPA)

A. Preparation of 1,3-dioxo-1,3-dihydroisobenzofuran-5-sulfonyl chloride and 1,3-dioxo-1,3-dihydroisobenzofuran-4-sulfonyl chloride

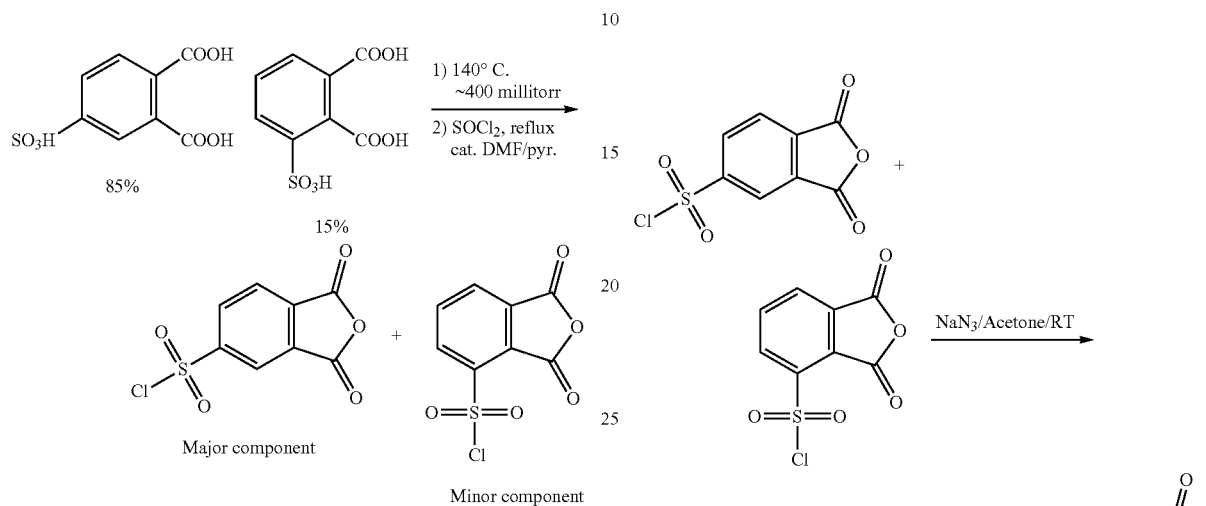

In a 500 mL round-bottom flask, 200 g of sulfophthalic acid aqueous (50 wt %) solution is placed. The solution is evaporated using a rotary evaporator at 95° C. until no more water is evaporated, and is subsequently placed in a Kugelrohr apparatus and heated under high vacuum (~400 millitorr) at ~140° C. until no more water is evaporated to yield 98 g of a viscous yellowish material. After cooling, thionyl chloride (200 mL) is added to the product with catalytic amounts of DMF (dimethyl formamide) (2 drops) and pyridine (2 drops). The flask is fitted with a reflux condenser connected to a nitrogen ($N_2$) line and the reaction mixture is heated to 90° C. (oil bath temperature) overnight. It takes about 1 hour to get a homogeneous solution. The reaction mixture is cooled down and excess thionyl chloride is removed under vacuum using a rotary evaporator. Dichloroethane is added and removed under vacuum (to help remove residual thionyl chloride) to give 95.42 g of pale yellow viscous material. The product is distilled using a Kugelrohr apparatus. Two fractions are isolated. The first fraction (67 g) contains 85% of the 4-isomer and 15% of the 3-isomer. The second fraction (17 g) contains 73% of the 4-isomer and 27% of the 3-isomer. The first fraction is crystallized twice from dichloromethane-hexanes solvent mixture to give 48.5 g of product as a mixture of the 4-isomer and the 3-isomer in 85%:15% ratio, respectively.

$^1$H NMR (major product) (400 MHz, $CD_2Cl_2$, 30° C.): δ 8.68 (dd, J=1.7, 0.9 Hz, 1H), 8.58 (dd, J=8.1, 1.7 Hz, 1H), 8.32 (dd, J=8.1, 0.7 Hz, 1H).

$^1$H NMR (minor product) (400 MHz, $CD_2Cl_2$, 30° C.): δ 8.53 (dd, J=7.9, 0.9 Hz, 1H), 8.41 (dd, J=7.7, 0.9 Hz, 1H), 8.23-8.15 (m, 1H).

$^{13}$C NMR (major product) (101 MHz, $CDCl_3$, 30° C.): δ 160.44, 160.11, 150.64, 135.97, 134.37, 132.62, 127.56, 124.52.

B. Synthesis of 4-Azidosulfonylphthalic Anhydride (ASPA)

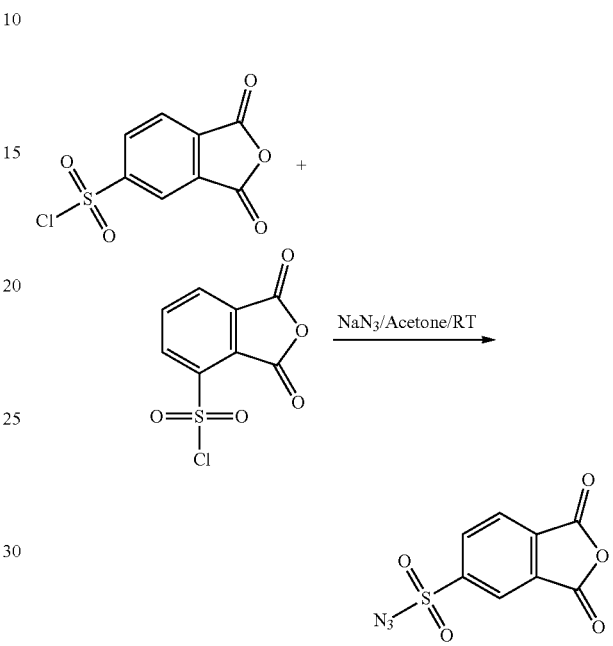

A mixture of 1,3-dioxo-1,3-dihydroisobenzofuran-5-sulfonyl chloride and 1,3-dioxo-1,3-dihydroisobenzofuran-4-sulfonyl chloride (35 g, 0.142 mol) is dissolved in acetone (500 mL). Solid $NaN_3$ (10.92 g, 0.168 mol) is added and the reaction mixture is stirred overnight under nitrogen. The reaction mixture is filtered from the sodium chloride byproduct using filter paper (some of the precipitate goes through the filter paper). The solvent is removed under vacuum and ethyl acetate (300 mL) is added. The sulfonyl azide product dissolves, whereas NaCl and any unreacted $NaN_3$ remains insoluble. The ethyl acetate solution is washed with water, and is subsequently washed with saturated aqueous sodium chloride solution and dried with anhydrous sodium sulfate and filtered. The solvent is removed under vacuum and the product is recrystallized twice from dichloromethane/hexanes to give 9.1 g of final product (yield=25.3%).

$^1$H NMR (500 MHz, acetone-$d_6$, 30° C.): δ 8.68-8.60 (m, 2H), 8.48-8.41 (m, 1H).

$^{13}$C NMR (126 MHz, acetone-$d_6$, 30° C.): δ 162.38, 162.07, 146.10, 137.21, 135.73, 133.89, 128.05, 125.17.

3. Materials

The materials used in the examples are provided in Table 1 below.

TABLE 1

| Material/Description | Properties | Source |
|---|---|---|
| NORDEL ™ IP 4725P | EPDM<br>ethylene = 70%* propylene = 25%*<br>ethylidene norbornene (ENB) = 5%*<br>density = 0.88 g/cc Mooney viscosity = 25 MU<br>crystallinity = 12% Tc = 36° C.<br>*Composition - amounts are shown in wt % based on total weight EPDM | The Dow Chemical Company |

TABLE 1-continued

| Material/Description | Properties | Source |
|---|---|---|
| maleic anhydride | melting point = 52-54° C. relative density = 1.48 g/cc boiling point = 200° C. vapor pressure = 0.33 hPa at 20° C. | Sigma Aldrich |
| 4-azidosulfonylphthalic anhydride | Decomposition temperature = 189° C. (DSC); Limiting impact energy as determined by the BAM Fall Hammer Test = 30-40 Joules; Predicted half-life (neat) at 210° C. (DSC, isoconversional analysis) = 36.3 sec; Predicted half-life (in ENGAGE ™ EG8400 blend at a 1.96 wt % concentration of 4-azidosulfonylphthalic anhydride) at 210° C. (DSC, isoconversional analysis) = 41.5 sec. | The Dow Chemical Company |
| Luperox ™ 101, 90% | 2,5 dimethyl 2,5-di-t-butylperoxy hexane boiling point = 55-57° C. at 9 hPa density = 0.877 g/cc at 25° C. flash point = 65° C. - closed up | Sigma Aldrich |
| ParaLux ™ 6001 | paraffinic process oil density = 0.8525-0.8692 kg/L @ 15° C. initial boiling point = 315° C. | Chevron |

4. Control Sample—Preparation of MAH-g-EPDM

NORDEL™ IP 4725P pellets (11.81 g control, 11.57 g comparative sample (CS-A) are weighed into 1 oz/30 mL Nalgene™ polypropylene wide mouth bottles with matching caps. The grafting reaction is performed using a DSM Xplore Micro Compounder (serial #15-10-8) with two double conical co-rotating detachable extruder screws, length: 150 mm, surface hardened to 1000 Vickers. The system has a control computer with USB communication cable and a manual piston feed hopper with a lid. Control/data logging software Xplore software V.2.01 is used. The temperature at the DSM Xplore instrument is set to 180° C. and the system is allowed to equilibrate. All processing is done under a light flow of nitrogen. The NORDEL™ IP 4725P pellets are added to the DSM instrument and fluxed at 20 rpm for 2 minutes after the hopper plug is secured. The desired amount of maleic anhydride (N/A for control, 0.399 wt %, 0.0481 g for CS-A) is added to the instrument via a dose bag (0.100 g for control, 0.199 g for CS-A) and the mixture is fluxed for 2 min. Subsequently, Luperox™ 101 (N/A for control, 0.0141 wt %, 0.0017 g CS-A) is added via a dose bag (0.090 g for control, 0.227 g for CS-A) and the mixture is fluxed for an additional 6 min with rpm=20 for the control. For CS-A, the screw speed is reduced to 10 rpm approximately 2 minutes after peroxide addition when the force reading approaches instrument overload values. The DSM Xplore instrument is stopped and the MAH-g-EPDM polymer is removed from the mixer while hot. Table 2 shows the characterization results from the synthesized control MAH-grafted EPDM-based polymer (MAH-g-EPDM).

A. MAH-g-EPDM—Grafting Levels of Maleic Anhydride (MAH) Determination

The grafting levels of MAH are determined via manual colorimetric titration. The MAH-g-EPDM sample (6.3 g) is added to 250 mL of stirring toluene and is let stirring over the course of two and a half days. Subsequently, the mixture is warmed with a hot plate while stirring until all of the polymer is dissolved. The polymer solution is precipitated into acetone (1 L). The MAH-grafted polymer is collected by filtration and is soaked in 600 mL of acetone for 15 min and filtered again. The polymer is subsequently dried in a vacuum oven at 80° C., overnight. Prior to the titration experiment, the purified polymer is dried in a nitrogen purged vacuum oven at 130° C. for one hour. Subsequently, 1 gram of the dried MAH-grafted polymer is dissolved in hot xylenes. The sample is titrated with 0.02 N tetrabutylammonium hydroxide in 50/50 methanol/toluene using bromothymol blue indicator to a constant blue color endpoint. The MAH-g-EPDM sample is titrated three times and the results are averaged.

TABLE 2

Characterization of MAH-g-EPDM Control Polymer

| Run# | wt % MAH (titration)[a] | GE (%) | $M_w^b$ | $M_n^b$ | PDI[b] | I2[c] |
|---|---|---|---|---|---|---|
| NORDEL ™ IP 4725P | — | — | 119,420 | 36,675 | 3.26 | 0.41 |
| NORDEL ™ IP 4725P processed in DSM at 180° C. | — | — | 113,840 | 35,365 | 3.22 | 0.56 |
| Comparative Sample A (CS-A) | 0.14 ± 0.005 | 36 ± 1 | 121,595 | 31,245 | 3.89 | 0.02[d] |

[a]Average of three measurements.

[b]High temperature GPC data is obtained on crude samples. The molecular weight data (Mw, Mn, PDI) may not represent the actual molecular weight of the polymer, as the MAH-g-EPDM may have crosslinked in the high temperature GPC instrument.

[c]I2 data is obtained on crude samples using a Melt Flow Jr. instrument from CEAST, which follows the ASTM D 1238 method.

[d]I2 is inversely proportional to viscosity. The lower melt index value of Comparative Sample A indicates that the viscosity of this sample is significantly higher than the inventive examples. Although the molecular weight measurement does not display a statistically significant difference in molecular weight values, the melt index values demonstrate that the vinyl groups in the EPDM sample are reacted to form a higher molecular weight sample. One reason that this molecular weight is not measured directly by the high temperature GPC is that any cross-linked material would not go into solution, and therefore could not be measured in the detector of the GPC instrument.

GE = grafting efficiency = ((wt % MAH grafted)/(wt % MAH added to the reaction)) * 100.

5. Examples—Preparation of SPA-g-EPDM via a DSM Micro Compounder

NORDEL™ IP 4725P pellets are weighed into 2 oz/60 mL glass jar with wide mouth and white Teflon™ seal lid. The desired weight of mineral oil is added. The contents of the jar are sealed and placed within a secondary polyethylene jug containing a pad with absorbent material. The blend contents are tumbled for 2 hours. After 2 hours, the desired amount of Irganox™ 1010 is added, followed by 4-azidosulfonylphthalic anhydride. The contents of the jar are sealed and placed within a secondary polyethylene jug containing a pad with absorbent material. The dry blend contents are tumbled on a roller overnight to uniformly distribute the azide compound onto the NORDEL™ IP 4725P (EPDM) pellets. The next day, the grafting reaction is performed using a DSM Xplore Micro Compounder (serial #15-10-8) with two double conical co-rotating detachable extruder screws, length: 150 mm, surface hardened to 1000 Vickers. The system has a control computer with USB communication cable and a manual piston feed hopper with a lid. Control/data logging software Xplore software V.2.01 is used. The temperature at the DSM Xplore instrument is set to 220° C. and the system is allowed to equilibrate. All melt processing is done under a light flow of nitrogen. The pre-mixed NORDEL™ IP 4725P pellets with 4-azidosulfonylphthalic anhydride are added to the DSM Xplore instrument and fluxed at 20 rpm for 5 minutes after the hopper plug is secured. The DSM Xplore instrument is stopped and the SPA-g-EPDM polymer is removed from the mixer while hot. Two first melt blending runs are performed under identical conditions and the synthetized SPA-grafted EPDM from the two runs are combined and used for analysis. Table 3 shows the material quantities utilized and Table 4 shows the characterization results from the synthesized SPA-grafted EPDM (SPA-g-EPDM) polymer.

A. SPA-g-EPDM—Grafting Levels of Maleic Anhydride (MAH) Determination

The grafting levels of MAH are determined via manual colorimetric titration. The SPA-g-EPDM sample (combined 4.26 g from run #1 and 4.12 g from run #2) is added to 250 mL of stirring toluene and is left stirring overnight. Subsequently, the mixture is warmed with a hot plate while stirring until the entire polymer is dissolved. The polymer solution is precipitated into acetone (1 L). The MAH-grafted polymer is collected by filtration. The precipitated solid is broken up, added to 1 L of stirring acetone, mixed for 15 min and subsequently filtered. The polymer is air dried over two days and then in a vacuum oven at 80° C., overnight. Prior to the titration experiment, the purified polymer is dried in a nitrogen purged vacuum oven at 130° C. for one hour. Subsequently, 1 gram of the dried MAH-grafted polymer is dissolved in hot xylenes. The sample is titrated with 0.02 N tetrabutylammonium hydroxide in 50/50 methanol/toluene using bromothymol blue indicator to a constant blue color endpoint. The SPA-g-EPDM sample is titrated three times and the results are averaged.

TABLE 3

Material quantities used in the grafting reactions of 4-azidosulfonylphthalic anhydride onto EPDM in pellets performed in a DSM Micro Compounder.

| Example # | NORDEL™ IP 4725P (g) | Mineral oil (wt %, g) | Irganox™ 1010 (wt %, g) | 4-azidosulfonylphthalic anhydride (wt %, g) | Equivalent wt % MAH | Jar residue (g)[a] |
|---|---|---|---|---|---|---|
| NORDEL™ IP 4725P control processed at 220° C. | 11.99 | — | — | — | — | — |
| Example 1 (run # 1) | 12.00 | 0.200, 0.0242 | 0.0496, 0.0060 | 0.502, 0.0607 | 0.194 | 0.026 |
| Example 1 (run # 2) | 12.00 | 0.198, 0.0240 | 0.0496, 0.0060 | 0.497, 0.0602 | 0.192 | 0.028 |

General grafting conditions: T = 220° C., rpm = 20, time = 5 min. NORDEL™ IP 4725P (pellet).
[a]Residue left in the jars after transferring the mixture of PE and sulfonyl azide anhydride molecule into the DSM micro compounder instrument.

TABLE 4

Characterization of SPA-g-EPDM Polymer.

| Run# | wt % MAH (titration)[a] | GE (%)[b] | $M_w$[c] | $M_n$[c] | PDI[c] | I2[d] |
|---|---|---|---|---|---|---|
| NORDEL™ IP 4725P processed at 220° C. | NA | NA | 117,155 | 36,520 | 3.21 | 0.52 |
| Example 1 (combined runs # 1 and # 2) | 0.15 ± 0.005 | 76 ± 3 | 118,245 | 37,480 | 3.15 | 0.35 |

[a]Average of three measurements.
[b]GE = grafting efficiency = ((wt % MAH grafted)/(Equivalent wt % MAH added to the reaction)) * 100.
[c]High temperature GPC data is obtained on crude samples (one measurement).
[d]I2 data is obtained on crude samples using a Melt Flow Jr. instrument from CEAST, which follows the ASTM D 1238 method.

6. Examples—Preparation of SPA-g-EPDM via a Coperion ZSK-25MC Twin-Screw Extruder The reactive extrusion of EPDM (NORDEL™ IP 4725P pellets) with 4-azidosulfonylphthalic anhydride is conducted on a Coperion ZSK-25MC twin-screw extruder. The extruder is equipped with a 25 mm twin-screw. The length to diameter ratio is 48. There are 11 independently controlled barrel sections with electric heating and water cooling. The temperature profile of extrusion is provided in Table 5. A predetermined amount of NORDEL™ IP 4725P EPDM pellets is weighed inside a fume hood and placed in a plastic bag, followed by a pre-determined amount of ParaLux™ 6001 oil. The bag is sealed and the mixture is tumble-mixed carefully. Subsequently, a pre-determined amount of 4-azidosulfonylphthalic anhydride is weighed inside a fume hood and added to the bag containing the EPDM and ParaLux™ 6001 oil, followed by the addition of a pre-determined amount of Irganox™ 1010. The mixture is then tumble-mixed carefully to distribute and coat the 4-azidosulfonylazide and Irganox™ 1010 onto the EPDM pellets. A total of 6.80 Kg of mixture is prepared. The composition of the mixture is 98.78 wt % EPDM, 0.10 wt % ParaLux™ 6001, 1.05 wt % 4-azidosulfonylphthalic anhydride, and 0.05 wt % Irganox™ 1010.

The mixture is carefully transferred to a K-Tron Model KCL24KQX4 loss-in-weight feeder and fed to the extruder hopper under nitrogen purge in the first barrel section. The extruder screw speed is 150 rpm. Correspondingly, the die pressure is 800 psi (5.51 MPa) and the motor torque load is in the range of 62-67%. The flow rate is maintained at 4.53 kg/h. The produced polymer melt is then pelletized using a GALA LPU underwater pelletization system. A two-hole die is used with 90° F. (~32.2° C.) water temperature and a cutter speed of 1000 rpm. Table 5 shows the barrel temperature profile for the twin-screw extruder for the reactive extrusion of EPDM with 4-azidosulfonylphthalic anhydride. Table 6 shows the material quantities utilized and Table 7 shows the characterization results from the synthesized SPA-grafted EPDM (SPA-g-EPDM) polymer.

TABLE 5

Barrel temperature profile for twin-screw extruder for the reactive extrusion of EPDM with 4-azidosulfonylphthalic anhydride.

| Barrel Zone | Temperature (° C.) |
|---|---|
| Zone #1 | 100 |
| Zone #2 | 120 |
| Zone #3 | 190 |
| Zone #4 | 241 |
| Zone #5 | 209 |
| Zone #6 | 210 |
| Zone #7 | 209 |
| Zone #8 | 202 |
| Zone #9 | 209 |
| Zone #10 | 210 |
| Zone #11 | 230 |

A. SPA-g-EPDM—Grafting Levels of Maleic Anhydride (MAH) Determination

The grafting levels of MAH are determined via manual colorimetric titration. The SPA-g-EPDM sample (~3 g) is added to 100 mL of stirring toluene. The mixture is warmed with a hot plate while stirring until all of the polymer is dissolved. The polymer solution is precipitated into acetone (300 mL). The SPA-grafted EPDM polymer is collected by filtration, washed with acetone, and dried in a vacuum oven at 80° C., overnight. Prior to the titration experiment, the purified polymer is dried in a nitrogen purged vacuum oven at 130° C. for one hour. Subsequently, approximately 1 gram of the dried SPA-grafted polymer is dissolved in hot xylenes. The sample is titrated with 0.02 N tetrabutylammonium hydroxide in 50/50 methanol/toluene using bromothymol blue indicator to a constant blue color endpoint. The SPA-g-EPDM sample is titrated three times and the results are averaged.

TABLE 6

Material quantities used in the grafting reactions of 4-azidosulfonylphthalic anhydride onto EPDM in pellets performed in a Coperion ZSK-25MC twin-screw extruder.

| Example # | NORDEL™ IP 4725P (g) | ParaLux™ oil (wt %, g) | Irganox™ 1010 (wt %, g) | 4-azidosulfonylphthalic anhydride$^a$ (wt %, g) | Equivalent wt % MAH |
|---|---|---|---|---|---|
| NORDEL™ IP 4725P control | Extruded sample from extruder purge | — | — | — | — |
| Example 2 | 6718.8 | 0.10, 6.97 | 0.05, 3.58 | 1.055, 75 | 0.408 |

$^a$Purity of 4-azidosufonylazide batch = 95.7%

TABLE 7

Characterization of SPA-g-EPDM Polymer.

| Run# | wt % MAH (titration)$^a$ | GE (%)$^b$ | $M_w$$^c$ | $M_n$$^c$ | PDI$^c$ | I2$^d$ |
|---|---|---|---|---|---|---|
| NORDEL™ IP 4725P | NA | NA | 119,665 | 37,135 | 3.22 | 0.44 |
| NORDEL™ IP 4725P processed in extruder | NA | NA | 121,125 | 37,275 | 3.25 | 0.45 |
| Example 2 | 0.27 ± 0.025 | 65 ± 6 | 122,205 | 34,350 | 3.56 | 0.18 |

$^a$Average of three measurements.
$^b$GE = grafting efficiency = ((wt % MAH grafted)/(Equivalent wt % MAH added to the reaction)) * 100.
$^c$High temperature GPC data is obtained on crude samples (one measurement).
$^d$I$_2$ data is obtained on crude samples using a Melt Flow Jr. instrument from CEAST, which follows the ASTM D 1238 method.

Not wishing to be bound by any particular theory, Applicant believes a heterophasic matrix containing SPA-g-EPDM discontinuous phase dispersed in a polar polymer continuous phase, in which a sulfonamide phthalic anhydride linkage (SPA) bonds all, or a portion of, the EPDM to all, or a portion of, the polar polymer will advantageously exhibit a reduction in the size of the discontinuous EPDM domains compared to compositions that lack a sulfonamide phthalic anhydride linkage (SPA) binding the EPDM to the continuous phase. The SPA bond is believed to minimize droplet coalescence of the EPDM discontinuous phase, thus ensuring smaller particle size distribution. Improved impact performance results from a smaller EPDM dispersed phase size.

It is specifically intended that the present disclosure not be limited to the embodiments and illustrations contained herein, but include modified forms of those embodiments including portions of the embodiments and combinations of elements of different embodiments as come within the scope of the following claims.

We claim:
1. The A composition comprising:
an ethylene/α-olefin/diene terpolymer;
a polar component that is a polar polymer selected from the group consisting of polyamide (nylon), ethylene/vinyl alcohol (EVOH) copolymer, polyurethane, polyacrylate, polyacrylonitrile, polycarbonate, polybuty- lene terephthalate (PBT), polyethylene terephthalate (PET), and combinations thereof; and a sulfonamide phthalic anhydride linkage (SPA) bonding the ethylene/α-olefin/diene terpolymer to the polar component.

2. The composition of claim 1 wherein the α-olefin of the ethylene/α-olefin/diene terpolymer is a $C_3$-$C_{12}$ α-olefin.

3. The composition of claim 1 wherein the diene is selected from the group consisting of 1,4-hexadiene, 1,9-decadiene, 4-methyl-1,4-hexadiene, 5-methyl-1,4-hexadiene, 1,5-cyclooctadiene, 1,6-octadiene, 1,7-octadiene, 7-methyl-1,6-octadiene, 3,7-dimethyl-1,6-octadiene, 3,7-dimethyl-1,7-octadiene, 5,7-dimethyl-1,6-octadiene, 3,7,11-trimethyl-1,6,10-octatriene, 6-methyl-1,5-heptadiene, 1,3-butadiene, 1,6-heptadiene, 1,8-nonadiene, 1,9-decadiene, 1,10-undecadiene, 1,5-cyclododecadiene, bicyclo[2.2.1]hepta-2,5-diene (norbornadiene), 5-ethylidene-2-norbornene, tetracyclododecene, dicyclopentadiene, 1,3-cyclopentadiene; 1,4-cyclohexadiene, vinyl norbornene, mixed isomers of dihydromyricene and dihydroocinene, tetrahydroindene, methyl tetrahydroindene, 5-methylene-2-norbornene (MNB); 5-propenyl-2-norbornene, 5-isopropylidene-2-norbornene, 5-(4-cyclopentenyl)-2-norbornene, 5-cyclohexylidene-2-norbornene, 5-vinyl-2-norbornene, 5-ethylidene-2-norbornene (ENB), 5-vinylidene-2-norbornene (VNB), 5-methylene-2-norbornene (MNB), and combinations thereof.

4. The composition of claim 1 wherein the ethylene/α-olefin/diene terpolymer is an ethylene/propylene/diene terpolymer (EPDM).

5. The composition of claim 1 wherein the ethylene/α-olefin/diene terpolymer is ethylene/propylene/5-ethylidene-2-norbornene terpolymer.

6. A composition comprising:
an ethylene/α-olefin/diene terpolymer;
a polar component; and
a sulfonamide phthalic anhydride linkage (SPA) bonding the ethylene/α-olefin/diene terpolymer to the polar component, wherein the sulfonamide phthalic anhydride linkage has the Structure (10)

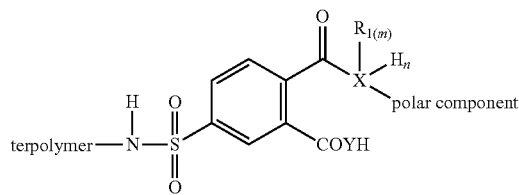

Structure (10)

wherein the nitrogen, N, is bound to a carbon, C, of the terpolymer;
X is selected from O, P, S, and N;
Y is selected from O, S, PH, PR, NH, and NR, and R is selected from an alkyl group and an aryl group;
$R_1$ is a $C_1$-$C_8$ alkyl group;
m and n each independently is 0 or 1 with the proviso when m=1, n=0
and when n=1, m=0.

7. A process comprising:
first melt blending an ethylene/α-olefin/diene terpolymer and 4-azidosulfonylphthalic anhydride at a temperature greater than or equal to the decomposition temperature of the 4-azidosulfonylphthalic anhydride to form a sulfonamide phthalic anhydride grafted ethylene/α-olefin/diene terpolymer;

second melt blending the sulfonamide phthalic anhydride grafted ethylene/α-olefin/diene terpolymer and a polar polymer selected from the group consisting of polyamide (nylon), ethylene/vinyl alcohol (EVOH) copolymer, polyurethane, polyacrylate, polyacrylonitrile, polycarbonate, polybutylene terephthalate (PBT), polyethylene terephthalate (PET), and combinations thereof; and forming a sulfonamide phthalic anhydride linkage between the ethylene/α-olefin/diene terpolymer and the polar polymer.

8. The process of claim 7 comprising:
second melt blending the sulfonamide phthalic anhydride grafted ethylene/α-olefin/diene terpolymer, a first polar polymer, and a second polar polymer that is different than the first polar polymer;
forming a first sulfonyl phthalic anhydride linkage between the ethylene/α-olefin/diene terpolymer and the first polar polymer; and
forming a second sulfonyl phthalic anhydride linkage between the ethylene/α-olefin/diene terpolymer and the second polar polymer.

9. The process of claim 8 comprising:
forming a polar polymer 1-SPA-polar polymer 2 linkage.

10. The composition of claim 6 wherein the α-olefin of the ethylene/α-olefin/diene terpolymer is a $C_3$-$C_{12}$ α-olefin.

11. The composition of claim 6 wherein the diene is selected from the group consisting of 1,4-hexadiene, 1,9-decadiene, 4-methyl-1,4-hexadiene, 5-methyl-1,4-hexadiene, 1,5-cyclooctadiene, 1,6-octadiene, 1,7-octadiene, 7-methyl-1,6-octadiene, 3,7-dimethyl-1,6-octadiene, 3,7-dimethyl-1,7-octadiene, 5,7-dimethyl-1,6-octadiene, 3,7,11-trimethyl-1,6,10-octatriene, 6-methyl-1,5-heptadiene, 1,3-butadiene, 1,6-heptadiene, 1,8-nonadiene, 1,9-decadiene, 1,10-undecadiene, 1,5-cyclododecadiene, bicyclo[2.2.1]hepta-2,5-diene (norbornadiene), 5-ethylidene-2-norbornene, tetracyclododecene, dicyclopentadiene, 1,3-cyclopentadiene; 1,4-cyclohexadiene, vinyl norbornene, mixed isomers of dihydromyricene and dihydroocinene, tetrahydroindene, methyl tetrahydroindene, 5-methylene-2-norbornene (MN B); 5-propenyl-2-norbornene, 5-isopropylidene-2-norbornene, 5-(4-cyclopentenyl)-2-norbornene, 5-cyclohexylidene-2-norbornene, 5-vinyl-2-norbornene, 5-ethylidene-2-norbornene (ENB), 5-vinylidene-2-norbornene (VNB), 5-methylene-2-norbornene (MNB), and combinations thereof.

12. The composition of claim 6 wherein the ethylene/α-olefin/diene terpolymer is an ethylene/propylene/diene terpolymer (EPDM).

13. The composition of claim 6 wherein the ethylene/α-olefin/diene terpolymer is ethylene/propylene/5-ethylidene-2-norbornene terpolymer.

14. The composition of claim 6 wherein the polar component is a polar polymer selected from the group consisting of polyamide (nylon), ethylene/vinyl alcohol (EVOH) copolymer, polyurethane, polyacrylate, polyacrylonitrile, polycarbonate, polybutylene terephthalate (PBT), polyethylene terephthalate (PET), and combinations thereof.

* * * * *